United States Patent
Gandras

(10) Patent No.: US 7,799,013 B2
(45) Date of Patent: Sep. 21, 2010

(54) PELVIC ARTERIAL CATHETER

(76) Inventor: Eric John Gandras, 29 Vanderbilt Dr., Great Neck, NY (US) 11020

( * ) Notice: Subject to any disclaimer, the term of this patent is extended or adjusted under 35 U.S.C. 154(b) by 1530 days.

(21) Appl. No.: 10/716,853

(22) Filed: Nov. 20, 2003

(65) Prior Publication Data

US 2005/0113801 A1    May 26, 2005

(51) Int. Cl.
*A61M 25/00* (2006.01)
(52) U.S. Cl. .......... 604/523; 604/525; 604/528
(58) Field of Classification Search .......... 604/264, 604/96.01, 164.01, 523–532, 95.01–95.05, 604/544, 275–279
See application file for complete search history.

(56) References Cited

U.S. PATENT DOCUMENTS

| | | | |
|---|---|---|---|
| 5,221,270 A | * | 6/1993 | Parker .......... 604/527 |
| 5,342,386 A | * | 8/1994 | Trotta .......... 606/194 |
| 5,800,413 A | * | 9/1998 | Swartz et al. .......... 604/528 |
| 6,030,369 A | * | 2/2000 | Engelson et al. .......... 604/264 |

* cited by examiner

*Primary Examiner*—Kevin C Sirmons
*Assistant Examiner*—Phillip Gray
(74) *Attorney, Agent, or Firm*—Patterson Thuente Christensen Pedersen, P.A.; Bruce A. Lev

(57) ABSTRACT

An improved angiographic catheter that allows selective catheterization of the bilateral pelvic arteries via a unilateral single common femoral arterial entry site for the purpose of introducing radioopaque iodinated contrast solutions for both diagnostic and therapeutic purposes. The catheter has an optimal length, specific tapered and curved regions, and a progressively tapering diameter along its length. The catheter is made from a hybrid of soft, flexible hydrophilic and reinforced materials to allow for conformational changes in order to accommodate to the variety of vascular anatomy encountered in clinical angiographic practice.

32 Claims, 2 Drawing Sheets

Fig. 2
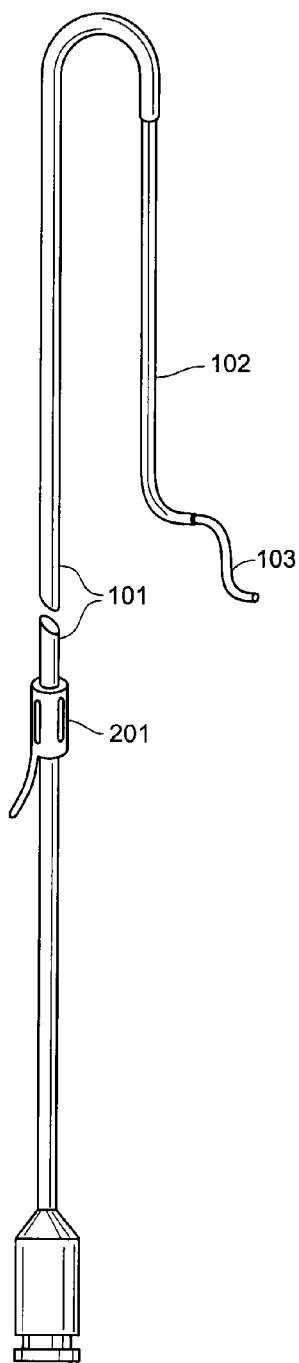
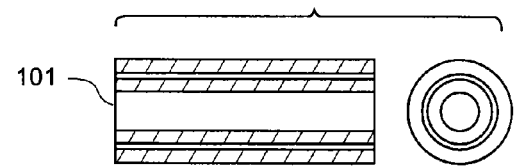
Fig. 2A
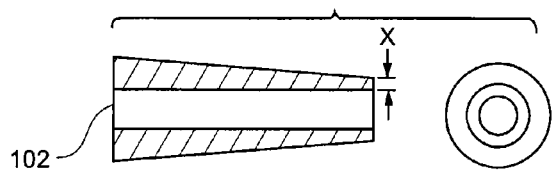
Fig. 2B
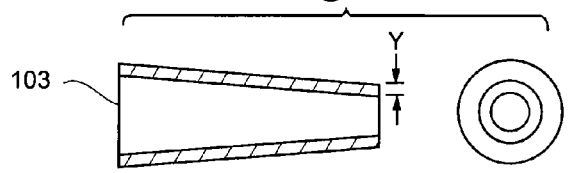
Fig. 2C

PELVIC ARTERIAL CATHETER

BACKGROUND OF THE INVENTION

Transcatheter arterial embolization of the pelvis has been performed for over 20 years in the treatment of pelvic trauma and post-partum hemorrhage. Previously it has been used as a neoadjuvant therapy prior to surgical myomectomy to minimize blood loss. In 1995 radiologists in France made the observation that bilateral embolization of the uterine arteries was associated with reduction of uterine fibroid tumor volumes and overall uterine volume. More importantly, patients who underwent this procedure experienced improvement or resolution of their symptoms approximately 80-90% of the time. Since that seminal observation, the procedure of uterine fibroid embolization has grown in popularity and has been used as a definitive therapy in peri-menopausal women for relief of symptoms of fibroid tumors of the uterus in over thousands of women worldwide. The procedure holds much promise as a non-surgical alternative to hysterectomy for the treatment of symptomatic myomata of the uterus.

Transcatheter arterial embolization of the pelvic visceral arteries for the above applications (and others) is performed in the vast majority of cases using a right common femoral arterial puncture site. The most common anatomy is that the arteries supplying the pelvic viscera arise from the anterior divisions of the internal iliac arteries, which arise from the common iliac arteries. In clinical practice, the arteries most commonly embolized are from the anterior division of the internal iliac artery. When performing catheterization of these pelvic visceral arteries via a right common femoral approach, it is usually technically easier to place the catheter into the contralateral visceral arteries than the ipsilateral visceral arteries due to the angle at which the vessels arise from the contralateral internal iliac artery. Traditionally it has been necessary to utilize several different catheters of varying shapes, lengths and materials to accomplish the catheterization of the bilateral pelvic visceral arteries prior to embolizing them and thus completing the procedure. Every catheter exchange increases the length and difficulty of the procedure. The risk of any interventional radiological procedure is directly proportional to its overall duration in time.

Every exchange increases the likelihood of vessel damage or non-target embolization.

SUMMARY OF THE INVENTION

Thus if a single catheter could achieve the objective of catheterizing both bilateral pelvic visceral arteries, such as the uterine arteries for uterine fibroid embolization, throughout the duration of the procedure it would decrease the length of the procedure and subsequently the overall risk to the patient . . . .

Furthermore, it would make the procedure technically easier and faster for the operator and thus represent an improvement in the current technology available. Several other observations while performing pelvic embolization procedures have been made by the author which would serve as further considerations in designing the ideal solitary catheter to achieve this end. The observations made are the following:

1. The pelvic visceral arteries are extremely prone to vasospasm and dissection following selective catheterization. Thus a catheter being introduced into them should be soft and atraumatic if one is to minimize the above complications from occurring in addition to using careful technique. The previous catheters which had been designed for pelvic arterial catheterization consist of polyethylene-type plastics which are quite stiff and exert a significant longitudinal force upon catheterizing the pelvic arteries. The tips also were not tapered significantly which may lead to intimal trauma.

2. Many embolic agents used, such as a suspension of polyvinyl alcohol particles (PVA) mixed in iodinated contrast, have a tendency to clump and occlude catheters smaller than 4 French (1.33 mm) in diameter along their entire length because of the increased peripheral resistance. When this occurs the catheter must be removed and catheterization of the vessel must be repeated. Thus the catheter ideally should be greater than or equal to 4 French in diameter over the majority of its length. However, because the pelvic visceral arteries are particularly prone to local trauma, the tip of the catheter should be as small as possible to minimize trauma, but not so small as to promote clumping of the embolic agent. Thus, a tapered system to maximize flow would seem to be optimal, from 5 French (1.66 mm) to 4 French (1.33 mm) along the catheter course. The tip should be soft and floppy, and a 3 French (1.00 mm) tip over a short length of the tip would be ideal to balance the flow of the embolic agent while minimizing trauma to the vessels.

3. Given the tortuosity of the vessels being catheterized, trackability becomes an important issue. In order to optimize trackability, a hydrophilic tip of the catheter would be a necessary feature.

4. Torquability decreases over the length of the catheter and the number of curves in both the catheter and blood vessels being catheterized. Thus, a braided catheter would confer an advantage in attempting to catheterize these pelvic vessels.

5. The primary curve of the catheter must take into account the anatomical variations in the angulation of the bifurcation of the aorta into the common iliac arteries and thus should be a gradual curve lest the catheter will kink at this level during contralateral catheterization of a shallow bifurcation. The diameter of this curve should be a minimum of 1.0 cm but no greater than 1.2 cm.

6. The secondary curve should take into account the angulations of the pelvic visceral arteries. It may arise 90 degrees from the shaft of the sidearm present from the level of the primary curve. It should ideally arise after a length between 14 cm and 17 cm beyond the end of the primary curve.

7. The length of the soft, floppy tip ("Elephant trunk") should allow catheterization of the vessels deep enough so that the tip lies safely within a pelvic arterial visceral branch, such as within the horizontal portion of the uterine artery, in order to facilitate flow-directed delivery of the embolic agent, minimizing non-target embolization of other vessels. The catheter tip diameter ideally should allow flow-directed delivery and should be smaller than the artery at that anatomic level to minimize occlusion of flow within the vessel secondary to catheterization. A short 3 French (1.00 mm) catheter tip between 2.0 cm and 8.0 cm would seem to be ideal accounting for the various lengths of the visceral pelvic vessels observed during numerous procedures performed. Utilization of microcatheters of 3 French over the entire catheter length has an unacceptably high clumping rate and furthermore these catheters are cumbersome to use, thus increasing procedure length. Their expensive price adds significantly to the overall cost of the procedure.

8. The overall length of traditional angiographic catheters for aortic catheterization may be too short to allow the length of catheter beyond the primary curve to be introduced along the distance from the aortic bifurcation to the pelvic visceral arteries. Thus the catheter length overall should be between 76 cm and 87 cm to achieve this goal. The longer the catheter length, the less responsive it is to steering and torquing.

9. The length of the distance from the primary to secondary curve ideally is between 14 cm and 17 cm based upon intra-procedure experience with various catheters.

10. The materials used in the overall novel design would need to have the characteristics of several different types of angiographic catheters currently available. It would need to be a synthesis of two different types of catheter materials: That of a firm, braided torquable shaft over the length of the catheter proximal to the primary curve such as polyurethane or polyethylene; and soft, floppy atraumatic material beyond the primary curve anywhere from the primary curve to the secondary curve to the tip of the catheter to minimize trauma and allow flow-directed delivery of embolic agent. As mentioned previously the tip should be hydrophilic to promote trackability. The materials should also be radioopaque. Beyond the secondary curve, it ideally would be made of the type of materials a standard 3 French coaxial microcatheter system is made of with a stainless steel reinforced polymer to minimize kinking over the length of the distal component. The catheter should be of a strength that will allow hand injection pressures of the embolic agent but need not be of a strength to allow mechanized power injection of radio opaque contrast within the arteries themselves as these are not essential to complete the procedure. Thus the catheter would be utilized with a 0.018 inch diameter or smaller guidewire which would serve to further limit trauma to the visceral arteries in contradistinction to the 0.035 inch diameter larger systems which are predominantly used today.

The above observations in the clinical setting have led to the development of a pelvic arterial catheter that would be ideal for catheterization of the bilateral pelvic arteries from a unilateral puncture site.

The pelvic arterial catheter (100) will allow catheterization of the bilateral pelvic visceral arteries, such as the uterine arteries, enlisting a single catheter using a solitary common femoral puncture site with minimal trauma to the blood vessel and maximal flow optimized for introducing embolic particles or radioopaque iodinated contrast and thus will represent a significant improvement in the existing technology available. The overall length should be greater than 76 cm but no more than 87 cm. The catheter diameter will taper from a 5 French (1.66 mm) component (101) to a 4 French (1.33 mm) component (102) to a 3 French (1.00 mm) outer diameter component (103) from end to end along its length. The 5 to 4 French transition will arise between 2.0 and 3.0 cm beyond the primary curve (104) approximately 61-64 cm beyond the proximal portion of the catheter, or hub (106). The 4 to 3 French transition will arise between 0.5 cm and 1.5 cm beyond the secondary curve (105). The length from the primary (104) to secondary curve (105) will be between 14.0 cm and 17.0 cm. The length beyond the secondary curve (105) will be between 2.5 cm and 8.0 cm. The radius of the primary curve (104) will be between 1.0 cm and 1.2 cm. It will begin between 59 and 62 cm beyond the catheter origin dependent upon the overall length of the catheter. The angle of the primary curve will be 360 degrees, with the flexibility of the material allowing conformational changes to adapt to varying anatomies so that the range will be between 180 and 420 degrees. The secondary curve (105) will have an angle between 90 and 100 degrees from the shaft of the catheter (102).

The materials utilized within the catheter may be a hybrid with fusion of the various components. The 5 French segment (101) should consist of polyethylene or polyurethane and should be braided with a metal such as stainless steel for added torquability. The 4 French segment (102) beyond the primary curve which is also the first tapered segment should be soft and hydrophilic to minimize longitudinal trauma to the vessels and facilitate catheterization. For example, a polyether block amide copolymer type of material could be employed. The materials beyond the secondary curve within the 3 French "Elephant trunk" component (103) would be similar to that of traditional microcatheter systems available today which use stainless steel reinforced plastics to minimize kinking. The catheter would have to be impregnated with a radioopaque material to be visible throughout its length during the procedure such as tungsten.

The transition between 5 French diameter (101) and 4 French diameter (102) components will begin between 2.0 and 3.0 cm beyond the primary curve. The catheter should be tapered at the tip its 3 French component (103) to 0.018 inches which will further serve to minimize trauma and vasospasm during the procedure.

An alternative to the 3 French "Elephant Trunk" component is to allow the catheter to taper to a 0.035 inch guidewire with the catheter length beyond the secondary curve to be no more than 1.0 cm to 2.0 cm. This will eliminate effectively the 3 French component but may allow catheterization safely if the 4 French component (102) is of a sufficient softness as to minimize longitudinal force when catheterizing the visceral arteries. Thus the "elephant trunk" could be considered and optional modification. In fact, a modular design could be considered to connect the 3 French component onto the tip of the 4 French component using screw threads such as a luer lock configuration or a flow switch type of adapter to allow the decision as to which configuration to use be determined by the physician depending upon the size and tortuosity of the vessels encountered at the time of the procedure.

The hub system will constitute the proximal origin of the catheter (106). It should be between 1.0 and 2.0 cm in length and have an inner diameter of 0.038 inches. It should consist of firm plastic such as polyurethane. A plastic straightener (201) will facilitate placement of the curved catheter over a straight guidewire for initial placement into the tubular structure of a blood vessel.

BRIEF DESCRIPTION OF THE DRAWINGS

FIG. 2 depicts schematically the catheter and cross-sectional views of the main three components in FIGS. 2A-C. FIG. 2A depicts the non-tapered first section which contains the primary curve in cross-section. This component is braided for added torque control.

Figure 1:
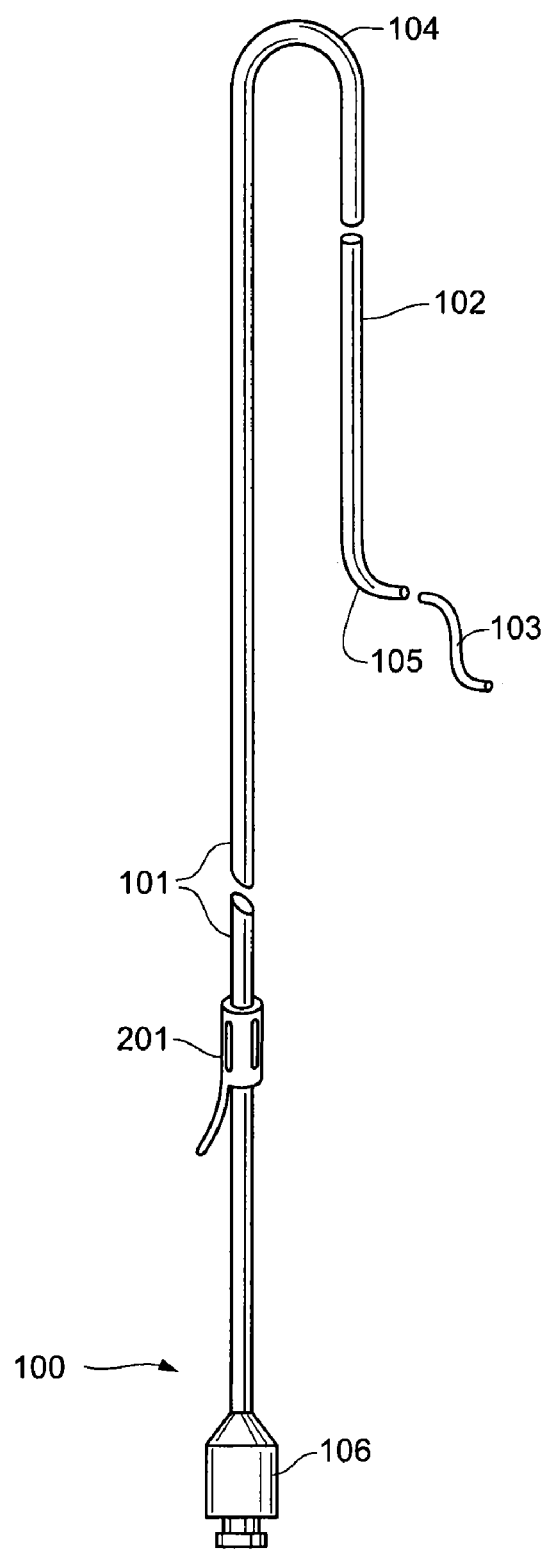
FIG. 1 depicts schematically the catheter not drawn to scale. The components are separated and telescoped.

Note the tapering of the individual components on the cross-sectional FIGS. 2B and 2C with respect to the outer and inner diameters. Note also the variable thickness of the walls of the two tapered components resulting from the differences in the degree of tapering between the outer and inner diameters. This is depicted schematically not to scale.

DETAILED DESCRIPTION OF PREFERRED EMBODIMENTS OF THE INVENTION

Referring to FIG. 1, an improved pelvic angiographic catheter 100 which will be between 76 and 87 cm in length. The majority of the length of the catheter consists of the 1.66 mm outer diameter component 101 which will be between 61 and 64 cm in length. 101 is made of a firm plastic material such as polyethylene which is braided with metal for torquability and to resist kinking. The primary curve of the catheter 104 falls within the 101 component between 2.0 and 3.0 cm proximal to the end of this component. The radius of 104 is between 1.0-1.2 cm in diameter and allows conformational changes between 180-420 degrees.

The next segment is the 1.33 mm outer diameter component 102 which is between 12 cm and 14 cm in length. This component is soft and hydrophilic to minimize longitudinal vectors of force when catheterizing the pelvic visceral arteries. The secondary curve 105 falls within the 102 component and starts between 11.5 cm and 13.5 cm beyond the origin of this segment. 105 exists at a 90-100 degree angle from the longitudinal shaft of 102.

The last segment is the 1.00 mm outer diameter component 103 ("elephant trunk") which is between 2.0 cm and 8.0 cm in length. This segment is soft and floppy but is reinforced with stainless steel to minimize kinking. It consists of soft plastic materials such as polyurethane or polyethylene used currently in microcatheters employed.

In FIG. 2, the individual components 101, 102 and 103 are depicted in cross-section. In addition the terminal hub 106 is again depicted as the origin of the catheter which will be made of hard plastic and extend between 1.0 and 2.0 cm in length. A straightener 201 is added to the diagram which is optional and would facilitate loading the catheter onto a straight guidewire.

The cross-sectional images of FIGS. 2A-2C depict the specifications of the tapers schematically. FIG. 2B depicts component 102, or the first tapered section, in cross-section. 102 tapers from 5 french (0.066 inches) to 4 french (0.053 inches) outer diameter and 0.038 inches to 0.035 inches inner diameter, which results in a variable thickness of the component such that the wall thickness (dimension X) tapers from beginning to end from 0.028 inches to 0.018 inches. FIG. 2C depicts component 103, or the second tapered section ("Elephant trunk"), in cross-section. 103 tapers from 4 french (0.053 inches) to 3 french (0.039 inches) outer diameter and 0.035 inches to 0.018 inches in inner diameter, which results in a variable thickness of the component such that the wall thickness (dimension Y) increases from beginning to end from 0.018 inches to 0.021 inches.

I claim:

1. A catheter adapted for use in pelvic angiographic procedures in which access to contralateral and ipsilateral branch arteries below the bifurcation of the internal iliac arteries is accomplished from a single common femoral arterial puncture site, the catheter comprising:
   a generally tubular structure defining only a single continuous lumen extending from a proximal end of the catheter to a distal end of the catheter;
   the generally tubular structure further defining a preformed primary curve located distal to the proximal end;
   the generally tubular structure further defining a first tapered section, the first tapered section being located distal to the primary curve and tapering such that the external diameter decreases from proximal to distal along the first tapered section;
   the generally tubular structure further defining a preformed secondary curve located distal to the primary curve and curving in a generally opposed direction to the primary curve; and
   wherein the first tapered section generally coincides in location with the secondary curve, further wherein a length from the primary curve to the secondary curve is between 14 cm and 17 cm, a length from the secondary curve to the catheter tip is between 3 cm and 8 cm; and further wherein an angle of the secondary curve is between 90 and 100 degrees from the shaft.

2. The catheter of claim 1 formed from a group of plastics that includes polyurethane, polyethylene and polyether block amide copolymer.

3. The catheter of claim 1, wherein a second tapered section tapers from an inner diameter of 0.035 inches to 0.018 inches, and wherein the outer diameter tapers from 4 french to 3 french.

4. The catheter of claim 1, wherein the overall length of the catheter is between 76 cm and 87 cm.

5. The catheter of claim 1, wherein the start of the first tapered section begins between 2.0 cm and 3.0 cm beyond the primary curve, and wherein the taper is from an inner diameter of 0.038 inches to 0.035 inches and an outer diameter of 5 French to 4 French.

6. The catheter of claim 1, wherein the start of a second tapered section begins between 0.5 cm and 1.5 cm from the secondary curve.

7. The catheter of claim 1, wherein the overall length of a second tapered section is between 2.0 cm and 8.0 cm.

8. The catheter of claim 1, wherein the radius of the primary curve is between 1.0 cm and 1.2 cm, and wherein the angle of said primary curve is within a range between 180 and 420 degrees.

9. The catheter of claim 1, wherein the catheter is formed from a braided material.

10. The catheter of claim 9, wherein the braided material is from a group that includes stainless steel.

11. The catheter of claim 1, wherein the catheter is impregnated with a radio opaque material.

12. The catheter of claim 11, wherein the radio opaque material is from a group that includes tungsten.

13. The catheter of claim 1, wherein the first tapered portion is made from a group of material that includes a polyether block amide copolymer.

14. The catheter of claim 1, wherein a hydrophilic coating is employed.

15. The catheter of claim 14, wherein the hydrophilic coating coats at least a portion of the catheter from the origin of the first tapered section to the tip.

16. The catheter of claim 1, including a hub at its origin.

17. The catheter of claim 16, wherein the length from the origin of the hub to the primary curve is between 59 cm and 62 cm.

18. The catheter of claim 16, wherein the hub is 1.0 to 2.0 cm in length and has an inner luminal diameter of 0.038 inches.

19. The catheter of claim 16, wherein the hub consists of polyurethane.

20. The catheter of claim 16, wherein the hub has an inner luminal diameter of 0.038 inches.

21. The catheter of claim 1 or 16, wherein a straightener extends on the outside of the catheter over a length between 2.0 cm and 3.0 cm.

22. The catheter of claim 21, wherein the straightener is made of polyurethane.

23. The catheter of claim 21, wherein the straightener is removable.

24. The catheter of claim 1 or 16, wherein the first tapered section is formed from a flexible material.

25. The catheter of claim 1 or 16, wherein the first tapered section is formed from an elastic material.

26. The catheter of claim 1 or 16, further comprising a second tapered section and wherein the second tapered section is formed from a soft material.

27. The catheter of claim 3 or 16, wherein the second tapered section is formed from a germ-retarding material.

28. The catheter of claim 3 or 16, wherein the thickness of the walls of the second tapered section changes along its length.

29. The catheter of claim 3 or 16, wherein the length of the second tapered section is at least 0.5 cm.

30. The catheter of claim 3 or 16, wherein the second tapered section is detachable.

31. The catheter of claim 3 or 16, wherein the second tapered section is formed separately from the rest of the catheter.

32. The catheter of claim 3 or 16, wherein the second tapered section is formed separately from the rest of the catheter and includes attachment means for removably attaching to the secondary curve.

* * * * *